United States Patent
Beutler et al.

(10) Patent No.: US 8,993,768 B2
(45) Date of Patent: Mar. 31, 2015

(54) TROPOLONE COMPOUNDS FOR TREATING OR PREVENTING RETROVIRAL INFECTION

(75) Inventors: John A. Beutler, Union Bridge, MD (US); Stuart F. J. LeGrice, Poolesville, MD (US); Craig Thomas, Gaithersburg, MD (US); Jian-Kang Jiang, Columbia, MD (US); Suhman Chung, Frederick, MD (US); Jennifer Wilson, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/116,423

(22) PCT Filed: May 10, 2012

(86) PCT No.: PCT/US2012/037208
§ 371 (c)(1),
(2), (4) Date: May 16, 2014

(87) PCT Pub. No.: WO2012/154904
PCT Pub. Date: Nov. 15, 2012

(65) Prior Publication Data
US 2014/0249181 A1 Sep. 4, 2014

Related U.S. Application Data
(60) Provisional application No. 61/484,779, filed on May 11, 2011.

(51) Int. Cl.
| | |
|---|---|
| *A61K 31/12* | (2006.01) |
| *C07D 233/60* | (2006.01) |
| *C07C 49/733* | (2006.01) |
| *C07C 225/18* | (2006.01) |
| *C07C 317/24* | (2006.01) |
| *C07C 323/22* | (2006.01) |
| *A61K 31/4453* | (2006.01) |
| *C07C 225/14* | (2006.01) |
| *C07D 295/088* | (2006.01) |
| *A61K 31/122* | (2006.01) |
| *A61K 31/4164* | (2006.01) |
| *A61K 45/06* | (2006.01) |
| *C07C 49/573* | (2006.01) |
| *C07D 233/64* | (2006.01) |
| *C07D 295/116* | (2006.01) |

(52) U.S. Cl.
CPC .......... *A61K 31/4453* (2013.01); *C07C 49/733* (2013.01); *C07C 225/14* (2013.01); *C07C 317/24* (2013.01); *C07C 323/22* (2013.01); *C07D 233/60* (2013.01); *C07D 295/088* (2013.01); *A61K 31/122* (2013.01); *A61K 31/4164* (2013.01); *A61K 45/06* (2013.01); *C07C 49/573* (2013.01); *C07D 233/64* (2013.01); *C07D 295/116* (2013.01); *C07C 2102/32* (2013.01)
USPC .......... 546/206; 548/341.1; 564/453; 568/31; 568/37; 568/43; 568/377; 514/319; 514/659; 514/690; 514/399

(58) Field of Classification Search
None
See application file for complete search history.

(56) References Cited

U.S. PATENT DOCUMENTS

| | | | |
|---|---|---|---|
| 4,450,150 A | 5/1984 | Sidman | |
| 2010/0152301 A1 | 6/2010 | Pommier et al. | |

FOREIGN PATENT DOCUMENTS

WO  WO 2007/065007 A3  6/2007

OTHER PUBLICATIONS

Bauman, et al., "Crystal engineering of HIV-1 reverse transcriptase for structure-based drug design," Nucleic Acids Research, 36(15): 5083-5092 (2008).
Budihas et al., "Selective Inhibition of HIV-1 reverse transcriptase-associated ribonuclease H activity by hydroxylated tropolones," Nucleic Acids Research, Oxford University Press, 33 (4) 1249-1256, 2005.
(Continued)

*Primary Examiner* — Nyeemah A Grazier
(74) *Attorney, Agent, or Firm* — Leydig, Voit & Mayer, Ltd.

(57) ABSTRACT

Disclosed are compounds that inhibit RNase H activity of retroviruses, for example, a compound of formula (I) wherein $R_1$, $R_2$, and $R_3$ are as described herein, as well as pharmaceutically acceptable salts, solvates, stereoisomers, and prodrugs thereof. Pharmaceutical compositions comprising such compounds, as well as methods of use, and treatment or prevention of infection by human immunodeficiency virus (HIV).

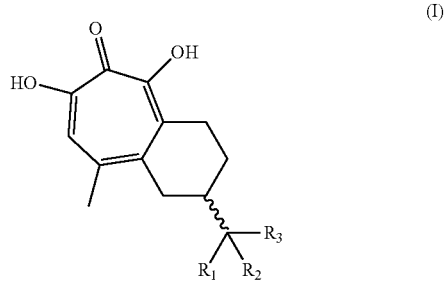

26 Claims, 3 Drawing Sheets

(56) References Cited

OTHER PUBLICATIONS

Figure 1:
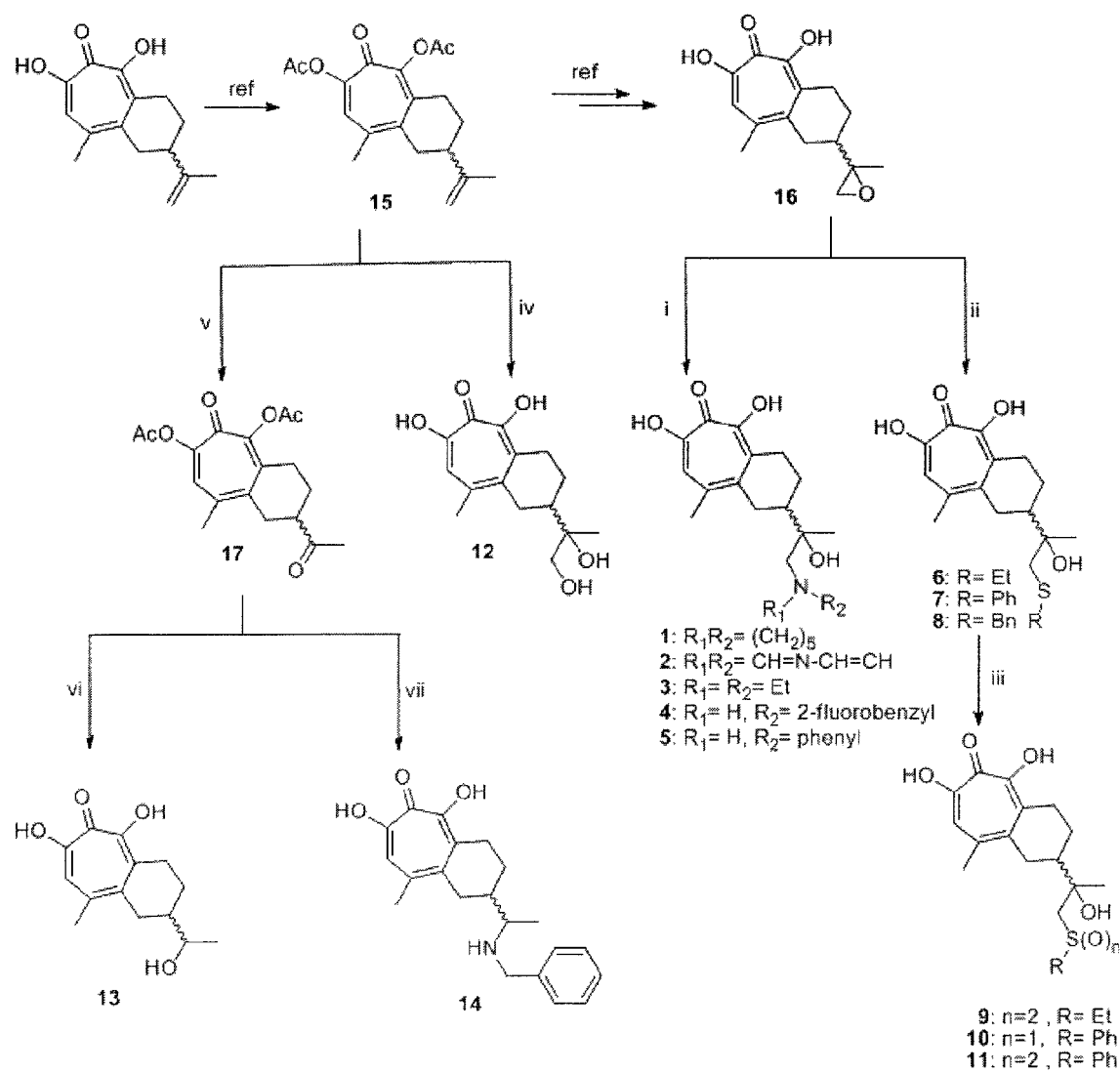

Chung S., et al., "Targeting HIV-1 Reverse Transcriptase-Associated Ribonuclease H Function," *Proceedings of 3rd Annual HIV/AIDS Conference in Eastern Europe and Central Asia* (Moscow, Oct. 2009).

Chung, et al., "Synthesis, Activity, and Structural Analysis of Novel α-hydroxytropolone inhibitors of Human Immunodeficiency Virus Reverse Transcriptawse-Associated Ribonuclease H," *Journal of Medicinal Chemisty*, 54(13): 4462-4473 (2011).

Chung, S. et al., "Targeting HIV-1 Reverse Transcriptase: a Coat with Many Pockets," Innovations in Pharmaceutical Technology, Dec. 2009, pp. 48-51 (2009) (published online at www.iptonline.com/biopharma/) (published Dec. 2009).

Das, et al., "High-resolution structures of HIV-1 reverse transcriptase/TMC278 complexes: Strategic flexibility explains potency against resistance mutations," *PNAS*, 105(5): 1466-1471 (2008).

Didierjean, J., et al., "Inhibition of HIV-1 Reverse Transcriptase, RNase H, and Integrase Activities by Hydroxytropolones," *Antimicrob. Agent Chemother.*, 49:4884-4894 (2005).

European Patent Office, International Preliminary Report on Patentability in International Application No. PCT/US2012/037208, 9 pages (Nov. 21, 2013).

European Patent Office, International Search Report in International Application No. PCT/US2012/037208, 6 pages (Aug. 2, 2012).

Gopalakrishnan, et al., "Human immunodeficiency virus type 1 reverse transcriptase: Spatial and temporal relationship between the polymerase and RNase H activities," *PNAS* 89(22): 10763-10767 (1992).

Kirst, et al. "Synthesis and Characterization of a Novel Inhibitor of an AminoGlycoside-Inactivating Enzyme," Journal of Antibiotics, 1651-1657 (1982).

Legrice, et al. "Rapid purification of homodimer and heterodimer HIV-1 reverse transcriptase by metal chelate affinity chromatography," Eur. J. Biocehm, 187(2): 307-314 (1990).

Wendeler, M., et al., "Vinylogous Ureas as a Novel Class of Inhibitors of Reverse Transcriptase-Associated Ribonuclease H Activity," *ACS Chem. Biol.*, 3:635-644 (2008).

FIGURE 3A
FIGURE 3B
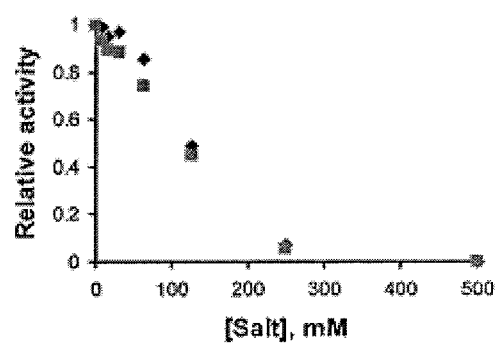
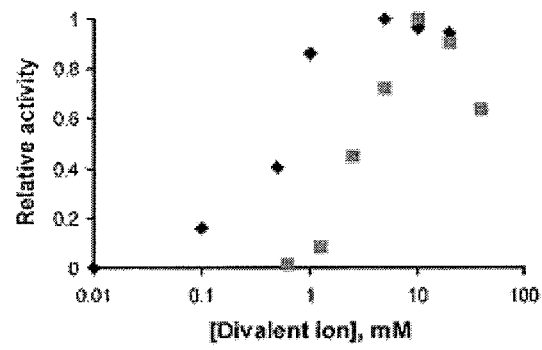

SEQUENCE LISTING

<160> NUMBER OF SEQ ID NOS: 6

<210> SEQ ID NO 1
<211> LENGTH: 29
<212> TYPE: RNA
<213> ORGANISM: Artificial Sequence
<220> FEATURE:
<223> OTHER INFORMATION: Synthethic

<400> SEQUENCE: 1
uuuuaaaaga aaaggggga cuggaaggg                                      29

<210> SEQ ID NO 2
<211> LENGTH: 39
<212> TYPE: DNA
<213> ORGANISM: Artificial Sequence
<220> FEATURE:
<223> OTHER INFORMATION: Synthetic

<400> SEQUENCE: 2

-continued

```
attagccctt ccagtccccc cttttctttt aaaaagtgg              39

<210> SEQ ID NO 3
<211> LENGTH: 28
<212> TYPE: RNA
<213> ORGANISM: Artificial Sequence
<220> FEATURE:
<223> OTHER INFORMATION: Synthetic

<400> SEQUENCE: 3
uuuccagaaa gagggggaa ugaaagac                           28

<210> SEQ ID NO 4
<211> LENGTH: 40
<212> TYPE: DNA
<213> ORGANISM: Artificial Sequence
<220> FEATURE:
<223> OTHER INFORMATION: Synthetic

<400> SEQUENCE: 4
gtggggtctt tcattccccc ctctttctgg aaactgaata             40

<210> SEQ ID NO 5
<211> LENGTH: 40
<212> TYPE: RNA
<213> ORGANISM: Artificial Sequence
<220> FEATURE:
<223> OTHER INFORMATION: Synthetic

<400> SEQUENCE: 5
ucaugcccug cuagcuacuc gauauggcaa uaagacucca             40

<210> SEQ ID NO 6
<211> LENGTH: 30
<212> TYPE: DNA
<213> ORGANISM: Artificial Sequence
<220> FEATURE:
<223> OTHER INFORMATION: Synthetic

<400> SEQUENCE: 6
tggagtctta ttgccatatc gagtagctag                        30
```

TROPOLONE COMPOUNDS FOR TREATING OR PREVENTING RETROVIRAL INFECTION

CROSS-REFERENCE TO RELATED APPLICATIONS

This patent application is the U.S. National Phase of International Patent Application No. PCT/US2012/037208, filed May 10, 2012, which claims the benefit of U.S. Provisional Patent Application No. 61/484,779, filed May 11, 2011, both of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,519 bytes-Byte ASCII (Text) file named "715540_ST25.txt," created on Nov. 8, 2013.

BACKGROUND OF THE INVENTION

Synthesis of double-stranded, integration-competent DNA in retroviruses proceeds through an RNA/DNA hybrid intermediate, whose (+) RNA genome must be removed to facilitate the second or (+)-strand DNA synthesis. Hybrid hydrolysis is mediated by the C-terminal ribonuclease H(RNase H) domain of the virus-coded reverse transcriptase (RT). In Human Immunodeficiency Virus (HIV), the etiological agent of acquired immunodeficiency syndrome (AIDS), RT is a p66/p51 heterodimer comprised of asymmetrically-organized subunits processed from the 165 kDa gag/pol polyprotein precursor. Abrogating RNase H function was demonstrated almost two decades ago to inhibit enzyme activity in vitro and virus replication in culture. Since these reports, however, there been a paucity of data on clinical trials with small molecule inhibitors, reflecting concerns over their toxicity, selectivity and cellular penetration.

The natural product α-hydroxytropolone, manicol (5,7-dihydroxy-2-isopropenyl-9-methyl-1,2,3,4-tetrahydro-benzocyclohepten-6-one) was previously demonstrated to potently and specifically inhibit the ribonuclease H(RNase H) activity of human immunodeficiency virus reverse transcriptase (HIV RT) in vitro. However, manicol was ineffective in reducing virus replication in culture, most likely due to toxicity caused by inhibition of cellular enzymes.

Therefore, there still exists an unmet need to find improved treatments for HIV infection by providing new retroviral RNase H inhibitors.

BRIEF SUMMARY OF THE INVENTION

In an embodiment, the present invention provides one or more compounds having the following General Formula I:

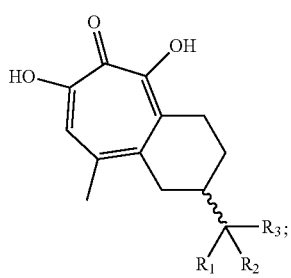

(I)

wherein $R_1$ is selected from the group consisting of H, heterocyclyl $C_1$-$C_6$ alkyl, $C_1$-$C_6$ alkylamino $C_1$-$C_6$ alkyl, $C_1$-$C_6$ dialkylamino $C_1$-$C_6$ alkyl, $C_6$-$C_{14}$ aryl $C_1$-$C_6$ alkylamino, $C_6$-$C_{14}$ aryl $C_1$-$C_6$ alkylamino $C_1$-$C_6$ alkyl, $C_6$-$C_{14}$ aryl amino $C_1$-$C_6$ alkyl, $C_1$-$C_6$ alkylthio $C_1$-$C_6$ alkyl, $C_6$-$C_{14}$ arylthio, $C_6$-$C_{14}$ arylthio $C_1$-$C_6$ alkyl, $C_6$-$C_{14}$ aryl $C_1$-$C_6$ alkylthio $C_1$-$C_6$ alkyl, $C_1$-$C_6$ alkylsulfonyl $C_1$-$C_6$ alkyl, $C_6$-$C_{14}$ arylsulfonyl $C_1$-$C_6$ alkyl, $C_6$-$C_{14}$ arylsulfinyl $C_1$-$C_6$ alkyl, hydroxy $C_1$-$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_6$-$C_{14}$ aryl, $C_6$-$C_{14}$ aryl $C_1$-$C_6$ alkyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydro, ureido, and aminocarbonyl; $R_2$ is H, OH, or $C_1$-$C_3$ alkyl; and $R_3$ is $C_1$-$C_6$ alkyl; or a pharmaceutically acceptable salt, solvate, stereoisomer, or a prodrug thereof.

In another embodiment, the present invention provides a pharmaceutical composition comprising at least one of the above identified compounds or a salt, solvate, stereoisomer, or a prodrug thereof, and a pharmaceutically acceptable carrier.

In still another embodiment, the present invention provides a pharmaceutical composition comprising at least one compound, salt, solvate, stereoisomer, or prodrug thereof, and at least one or more other antiviral compounds, and a pharmaceutically acceptable carrier.

In another embodiment, the present invention provides a method of treating or preventing a retroviral infection in a subject comprising administering an effective amount of at least one of the above identified compounds, or a salt, solvate, stereoisomer, or prodrug thereof.

In a further embodiment, the present invention provides a method for inhibition of replication of human immunodeficiency virus (HIV) in a subject comprising administering to the subject, an effective amount of at least one of the above identified compounds, or a salt, solvate, stereoisomer, or prodrug thereof.

In another embodiment, the present invention provides a method for inhibition of ribonuclease H (RNase H) in a subject infected with HIV comprising administering to the subject, an effective amount of at least one of the above identified compounds, or a salt, solvate, stereoisomer, or prodrug thereof.

BRIEF DESCRIPTION OF THE SEVERAL VIEWS OF THE DRAWING(S)

FIG. 1 is a reaction scheme depicting the various syntheses of Compounds 1-14 in accordance with an embodiment of the invention. Conditions and reagents: i) $NHR_1R_2$, $LiClO_4$, $CH_3CH$, 80° C.; ii) a) PhSH, $Et_3N$, THF, reflux; b) EtSH or BnSH, NaH, MeOH, r.t.; iii) mCPBA, DCM; iv) $OsO_4$, N-methylmorpholine oxide, acetone/$H_2O$; v) $OsO_4$, $NaIO_4$, $NaHCO_3$, t-BuOH/$H_2O$; vi) $NaBH_4$, MeOH, reflux; vii) $BnNH_2$, $NaBH(OAc)_3$, 1,2 dichloroethane.

Figure 2A:
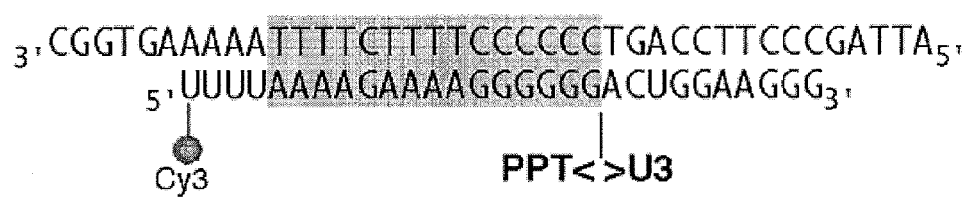
Figure 2B:
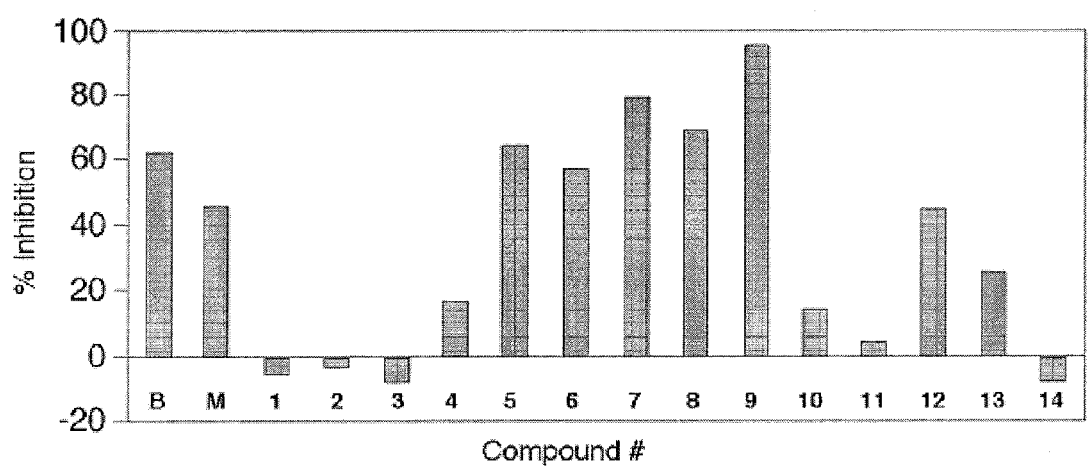

FIG. 2 depicts inhibition of RNase H-mediated release of the HIV-1 PPT primer from (+) RNA by the compounds of the present invention. FIG. 2A depicts a schematic model of RNA/DNA substrate, indicating the RNase H cleavage site at the PPT/U3 junction (< >). The PPT is indicated by the shaded box. FIG. 2B depicts the quantification of PPT cleavage data. All inhibitors were evaluated at 20 μM.

FIG. 3 displays the characterization of wild type and $D^{524}N$, RNase H-deficient XMRV RT. FIG. 3A depicts monovalent cation requirement of wild-type RT. (■), $K^+$, (♦), $Na^+$; FIG. 3B depicts the divalent cation requirement. (♦) $Mn^{++}$, (■), $Mg^{++}$.

DETAILED DESCRIPTION OF THE INVENTION

In an embodiment, the present invention provides one or more compounds having the following General Formula I:

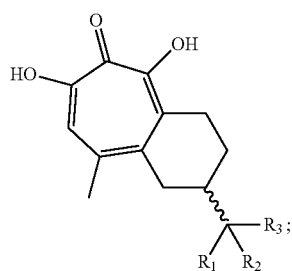

(I)

wherein $R_1$ is selected from the group consisting of H, heterocyclyl $C_1$-$C_6$ alkyl, $C_1$-$C_6$ alkylamino $C_1$-$C_6$ alkyl, $C_1$-$C_6$ dialkylamino $C_1$-$C_6$ alkyl, $C_6$-$C_{14}$ aryl $C_1$-$C_6$ alkylamino, $C_6$-$C_{14}$ aryl $C_1$-$C_6$ alkylamino $C_1$-$C_6$ alkyl, $C_6$-$C_{14}$ aryl amino $C_1$-$C_6$ alkyl, $C_1$-$C_6$ alkylthio $C_1$-$C_6$ alkyl, $C_6$-$C_{14}$ arylthio, $C_6$-$C_{14}$ arylthio $C_1$-$C_6$ alkyl, $C_6$-$C_{14}$ aryl $C_1$-$C_6$ alkylthio $C_1$-$C_6$ alkyl, $C_1$-$C_6$ alkylsulfonyl $C_1$-$C_6$ alkyl, $C_6$-$C_{14}$ arylsulfonyl $C_1$-$C_6$ alkyl, $C_6$-$C_{14}$ arylsulfinyl $C_1$-$C_6$ alkyl, hydroxy $C_1$-$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_6$-$C_{14}$ aryl, $C_6$-$C_{14}$ aryl $C_1$-$C_6$ alkyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydro, ureido, and aminocarbonyl; $R_2$ is H, OH, or $C_1$-$C_3$ alkyl; and $R_3$ is $C_1$-$C_6$ alkyl; or a pharmaceutically acceptable salt, solvate, stereoisomer, or a prodrug thereof.

In an embodiment, the present invention provides one or more compounds having the following General Formula I, set forth above, wherein $R_1$ is selected from the group consisting of heterocyclyl $C_1$-$C_6$ alkyl, $C_1$-$C_6$ alkylamino $C_1$-$C_6$ alkyl, $C_1$-$C_6$ dialkylamino $C_1$-$C_6$ alkyl, $C_6$-$C_{14}$ aryl $C_1$-$C_6$ alkylamino, $C_6$-$C_{14}$ aryl $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_6$-$C_{14}$ aryl $C_1$-$C_6$ alkylthio $C_1$-$C_6$ alkyl, $C_1$-$C_6$ alkylsulfonyl $C_1$-$C_6$ alkyl, $C_6$-$C_{14}$ arylsulfonyl $C_1$-$C_6$ alkyl, $C_6$-$C_{14}$ arylsulfinyl $C_1$-$C_6$ alkyl, hydroxy$C_1$-$C_6$ alkyl group, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, guanidine, aldehydro, ureido, and aminocarbonyl.

In another embodiment, the present invention provides one or more compounds having the following General Formula I, set forth above, wherein $R_1$ is $C_1$-$C_6$ dialkylamino $C_1$-$C_6$ alkyl.

In a further embodiment, the present invention provides one or more compounds having the following General Formula I, set forth above, wherein $R_1$ is heterocyclyl $C_1$-$C_6$ alkyl.

In accordance with an embodiment, the present invention provides one or more compounds having the following General Formula I, set forth above, wherein $R_1$ is $C_6$-$C_{14}$ aryl, $C_1$-$C_6$ alkylamino, or $C_1$-$C_6$ alkyl, wherein each of which is optionally substituted with halo.

In accordance with another embodiment, the present invention provides one or more compounds having the following General Formula I, set forth above, wherein $R_1$ is $C_6$-$C_{14}$ aryl amino $C_1$-$C_6$ alkyl.

In accordance with a further embodiment, the present invention provides one or more compounds having the following General Formula I, set forth above, wherein $R_1$ is $C_1$-$C_6$ alkylthio $C_1$-$C_6$ alkyl.

In an embodiment, the present invention provides one or more compounds having the following General Formula I, set forth above, wherein $R_1$ is $C_6$-$C_{14}$ arylthio.

In another embodiment, the present invention provides one or more compounds having the following General Formula I, set forth above, wherein $R_1$ is $C_6$-$C_{14}$ aryl $C_1$-$C_6$ alkylthio $C_1$-$C_6$ alkyl.

In accordance with an embodiment, the present invention provides one or more compounds having the following General Formula I, set forth above, wherein $R_1$ is $C_1$-$C_6$ alkylsulfonyl $C_1$-$C_6$ alkyl.

In accordance with another embodiment, the present invention provides one or more compounds having the following General Formula I, set forth above, wherein $R_1$ is $C_6$-$C_{14}$ arylsulfinyl $C_1$-$C_6$ alkyl.

In accordance with a further embodiment, the present invention provides one or more compounds having the following General Formula I, above, wherein $R_1$ is $C_6$-$C_{14}$ arylsulfonyl $C_1$-$C_6$ alkyl.

In an embodiment, the present invention provides one or more compounds having the following General Formula I, set forth above, wherein $R_1$ is hydroxy $C_1$-$C_6$ alkyl.

In yet another embodiment the present invention provides one or more compounds having the following General Formula I, set forth above, wherein $R_1$ is H, $R_2$ is OH and $R_3$ is $CH_3$.

In still a further embodiment, the present invention provides one or more compounds having the following General Formula I, set forth above, wherein $R_1$ is $C_6$-$C_{14}$ aryl $C_1$-$C_6$ alkylamino, $R_2$ is H and $R_3$ is $CH_3$.

In an embodiment, the present invention provides one or more compounds having the following General Formula I, set forth above, wherein $R_2$ is OH and $R_3$ is $CH_3$.

In another embodiment, the present invention provides at least one or more compounds selected from the group consisting of:

Compound 1
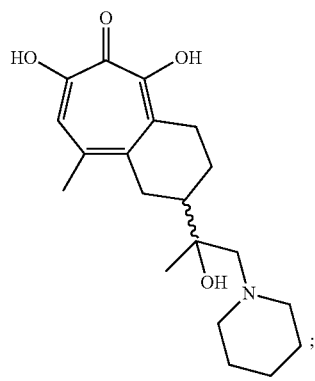
Compound 2
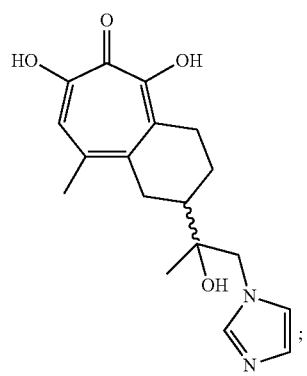
Compound 3
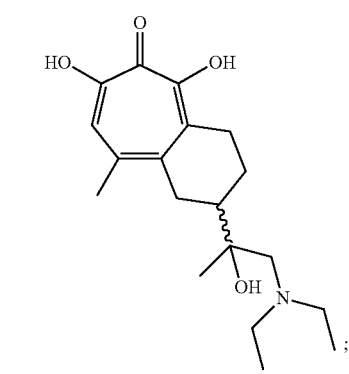
Compound 4
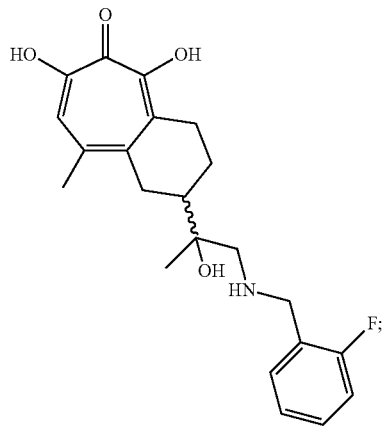
Compound 5
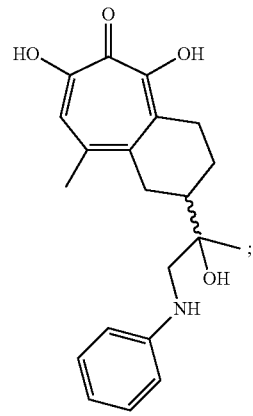
Compound 6
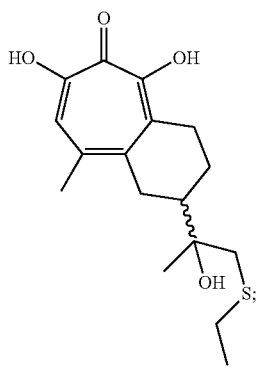
Compound 7
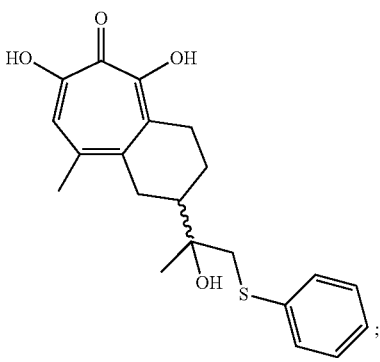
Compound 8
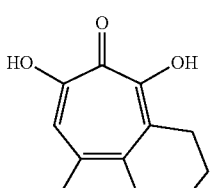

Compound 9

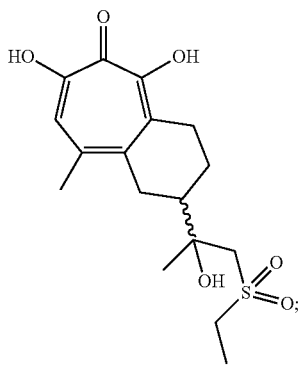

Compound 10

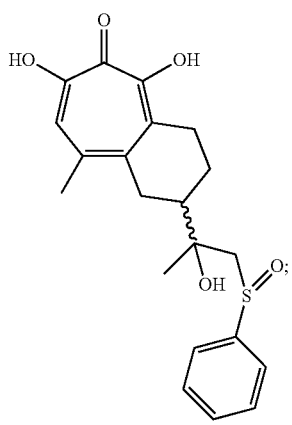

Compound 11

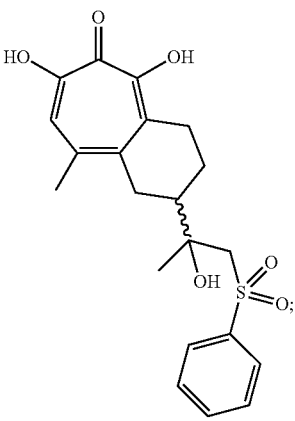

Compound 12

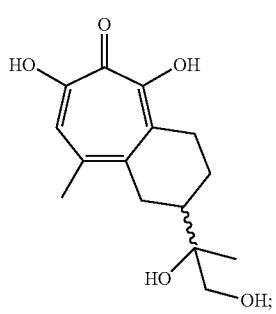

Compound 13

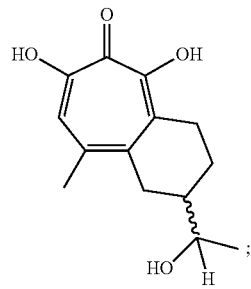

Compound 14

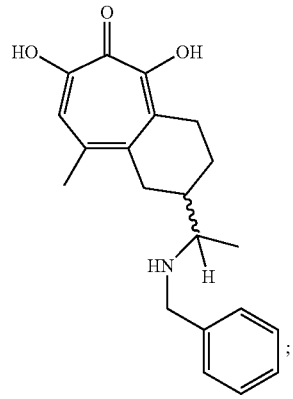

and pharmaceutically acceptable salts, solvates, stereoisomers, or prodrugs thereof.

In an embodiment, the present invention provides a RNase H inhibitor having the following General Formula I:

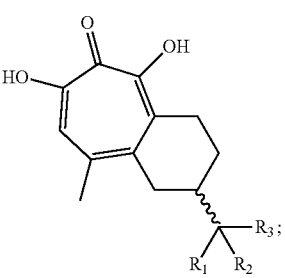

wherein $R_1$ is selected from the group consisting of H, heterocyclyl $C_1$-$C_6$ alkyl, $C_1$-$C_6$ alkylamino $C_1$-$C_6$ alkyl, $C_1$-$C_6$ dialkylamino $C_1$-$C_6$ alkyl, $C_6$-$C_{14}$ aryl $C_1$-$C_6$ alkylamino, $C_6$-$C_{14}$ aryl $C_1$-$C_6$ alkylamino $C_1$-$C_6$ alkyl, $C_6$-$C_{14}$ aryl amino $C_1$-$C_6$ alkyl, $C_1$-$C_6$ alkylthio $C_1$-$C_6$ alkyl, $C_6$-$C_{14}$ arylthio, $C_6$-$C_{14}$ arylthio $C_1$-$C_6$ alkyl, $C_6$-$C_{14}$ aryl $C_1$-$C_6$ alkylthio $C_1$-$C_6$ alkyl, $C_1$-$C_6$ alkylsulfonyl $C_1$-$C_6$ alkyl, $C_6$-$C_{14}$ arylsulfonyl $C_1$-$C_6$ alkyl, $C_6$-$C_{14}$ arylsulfinyl $C_1$-$C_6$ alkyl, hydroxy $C_1$-$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_6$-$C_{14}$ aryl, $C_6$-$C_{14}$ aryl $C_1$-$C_6$ alkyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydro, ureido, and aminocarbonyl; $R_2$ is H, OH, or $C_1$-$C_3$ alkyl; and $R_3$ is $C_1$-$C_6$ alkyl; or a pharmaceutically acceptable salt, solvate, stereoisomer, or prodrug thereof.

In another embodiment, the present invention provides a RNase H inhibitor selected from the group consisting of compounds 1-14 set forth above, or pharmaceutically acceptable salts, solvates, stereoisomers or prodrugs thereof.

In another embodiment, the present invention provides a pharmaceutical composition comprising at least one of the identified compounds set forth above or a salt, solvate, stereoisomer, or prodrug thereof, and a pharmaceutically acceptable carrier.

In another embodiment, the present invention provides a pharmaceutical composition comprising of at least one of the identified compounds set forth above or a salt, solvate, stereoisomer, or prodrug thereof, and a pharmaceutically acceptable carrier, and at least one or more other antiviral compounds. In a further embodiment, the antiviral compounds include nucleoside reverse transcriptase inhibitors (NRTI), non-nucleoside reverse transcriptase inhibitors (NNRTI), integrase inhibitors, fusion inhibitors and protease inhibitors.

In an embodiment, the present invention provides a method of treating or preventing a retroviral infection in a subject comprising administering to a subject, pharmaceutical composition comprising an effective amount of at least one or more of the identified compounds set forth above or a salt, solvate, stereoisomer, or prodrug thereof, and an effective amount of at least one or more other antiviral compounds.

In yet another embodiment, the present invention provides a method of inhibiting HIV replication in a subject comprising administering to a subject a pharmaceutical composition comprising an effective amount of at least one or more of the identified compounds set forth above or a salt, solvate, stereoisomer, or prodrug thereof. In accordance with the invention, in a further embodiment, the invention provides a method of inhibiting HIV replication in a subject comprising administering to a subject a pharmaceutical composition comprising an effective amount of at least one or more of the identified compounds set forth above, or a salt, solvate stereoisomer, or prodrug thereof, and an effective amount of at least one or more other antiviral compounds.

In another embodiment, the present invention provides a method of inhibiting HIV replication in a host cell comprising contacting the host cell with a pharmaceutical composition comprising an effective amount of at least one or more of the identified compounds set forth above, or a salt, solvate, stereoisomer, or prodrug thereof. In accordance with the invention, in a further embodiment, the invention provides a method of inhibiting HIV replication in a host cell comprising contacting the host cell with a pharmaceutical composition comprising an effective amount of at least one or more of the identified compounds set forth above, or a salt, solvate, stereoisomer, or prodrug thereof, and an effective amount of at least one or more other antiviral compounds.

In an embodiment, the present invention provides one or more of the identified compounds set forth above, or a salt, solvate, stereoisomer, or prodrug thereof, for use in treating or preventing a retroviral infection, inhibiting HIV replication, or inhibiting RNaseH activity of HIV.

As used herein, the term "antiviral compound" includes classes of drugs suitable for use in treating viral infections in vivo and/or in vitro. In particular, the term "antiviral compound" in the present invention, also means an "antiretroviral compound" suitable for use in treating retrovirus infections in vivo and/or in vitro. Examples of classes of antiviral compounds include NRTIs, NNRTIs, protease inhibitors, fusion or entry inhibitors, and integrase inhibitors.

In accordance with an embodiment of the present invention, examples of NRTIs include, but are not limited to, for example, lamivudine, abacavir, zidovudine, stavudine, didanosine, emtricitabine, and tenofovir.

In accordance with another embodiment of the present invention, examples of NNRTIs include, but are not limited to, for example, delavirdine, efavirenz, etravirine, rilpilvirine and nevirapine.

In accordance with an embodiment of the present invention, examples of protease inhibitors include, but are not limited to, for example, amprenavir, fosamprenavir, atazanavir, darunavir, indinavir, lopinavir, nelfinavir, ritonavir, saquinavir, and tipranavir.

In accordance with a further embodiment of the present invention, examples of fusion or entry inhibitors include, but are not limited to, for example, enfuvirtide and maraviroc.

In accordance with an embodiment of the present invention, examples of integrase inhibitors include, but are not limited to raltegravir, elvitegravir, and dolutegravir.

As used herein, examples of the term "alkyl" preferably include a $C_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include $C_{2-6}$ alkynyl (e.g., ethynyl, propargyl, 1-butynyl, 2-butynyl, 3-butynyl, 1-hexynyl, etc.) and the like.

Examples of the term "cycloalkyl" preferably include a $C_{3-8}$ cycloalkyl (e.g., a cyclopropyl, cyclobutyl, cyclopentyl, cyclohexyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The term "arylaminoalkyl" means an aryl group linked to an alkyl group via a nitrogen atom. An example of a preferred arylaminoalkyl is a $C_6$-$C_{14}$ aryl amino $C_1$-$C_6$ alkyl group.

The terms "alkylthio," "alkenylthio" and "alkynylthio" mean a group consisting of a sulphur atom bonded to an alkyl-, alkenyl- or alkynyl-group, which is bonded via the sulphur atom to the entity to which the group is bonded.

The terms "arylthio" means an aryl group with sulfur bonded thereto and further attached via the sulfur atom to another group. The term "aryl alkylthio alkyl" means an aryl group linked via an alkyl group to a sulfur atom, and wherein the sulfur atom is linked to another alkyl group which is linked to another group.

In addition, the present invention also encompasses prodrug compounds of these compounds and metabolite compounds as equivalent compounds besides the compounds represented by the above-mentioned General Formula I, set forth above. A "prodrug" is a derivative of the compound of the present invention having a group which may be decomposed chemically or metabolically and after administered to a living body, it goes through a chemical change to a compound which has an activity as a drug and exhibits its original pharmacological effect, and complexes and salts not by a covalent bond are included.

A prodrug is used for improving absorption upon oral administration or targeting to a target site. Moieties to be modified for forming a prodrug include reactive functional groups such as hydroxyl, carboxyl, amino, and thiol. Specific examples of the modifying group for hydroxyl include an acetyl, propionyl, isobutyryl, pivaloyl, benzoyl, 4-methylbenzoyl, dimethylcarbamoyl, sulfo, etc. Specific examples of the modifying group for carboxyl include ethyl, pivaloyloxymethyl, 1-(acetyloxy)ethyl, 1-(ethoxycarbonyloxy)ethyl, 1-(cyclohexyloxycarbonyloxy)ethyl, carboxylmethyl, methyl (5-methyl-2-oxo-1,3-dioxol-4-yl), phenyl, o-tolyl, etc. Specific examples of the modifying group for amino include a hexylcarbamoyl, 3-methylthio-1-(acetylamino)propylcarbonyl, 1-sulfo-1-(3-ethoxy-4-hydroxyphenyl)methyl, methyl(5-methyl-2-oxo-1,3-dioxol-4-yl), etc.

In addition, the above-mentioned compounds represented by General Formula I, may have various isomers. For example, E form and Z form are present as geometric isomers, and when an asymmetric carbon atom exists, enantiomer and diastereomer as stereoisomers based thereon exist, and a tautomer can exist.

The wavy bond depicted in the structures set forth herein is intended to mean that the structures represent enantiomers, racemates, and/or diasteromers. For example, the structure: $C_A \sim\!\sim\!\sim C_B$, when carbon atoms $C_A$ and $C_B$ are both chiral, represents all possible combinations of the structure. The aforesaid structure represents $(R_A R_B)$, $(R_A S_B)$, $(S_A R_B)$, and $(S_A S_B)$, wherein $R_A$, $R_B$, etc. represent the configuration about $C_A$ and $C_B$, respectively.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

As defined herein, in one or more embodiments, "contacting" means that the one or more compounds of the present invention are introduced into a sample having at least one retrovirus, including for example, HIV, and appropriate enzymes or reagents, in a test tube, flask, tissue culture, chip, array, plate, microplate, capillary, or the like, and incubated at a temperature and time sufficient to permit binding of the at least one compounds of the present invention to interact with RNase H.

In a further embodiment, the present invention provides a method of treating or preventing retroviral infection in a subject, the method comprising administering to the subject, a pharmaceutical composition comprising at least one compound of the present invention, and at least one other compound suitable for use in treating a retroviral infection, with a pharmaceutically acceptable carrier, in an effective amount to inhibit, suppress or treat symptoms of the retroviral infection.

In an embodiment, the pharmaceutical compositions of the present invention comprise the compounds of the present invention together with a pharmaceutically acceptable carrier.

Embodiments of the invention include a process for preparing pharmaceutical products comprising the compounds, salts, solvates or stereoisomers thereof. The term "pharmaceutical product" means a composition suitable for pharmaceutical use (pharmaceutical composition), as defined herein. Pharmaceutical compositions formulated for particular applications comprising the RNase H inhibitors of the present invention are also part of this invention, and are to be considered an embodiment thereof.

As used herein, the term "treat," as well as words stemming therefrom, includes preventative as well as disorder remitative treatment. The terms "reduce", "suppress" and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s), and one which has little or no detrimental side effects or toxicity under the conditions of use. Examples of the pharmaceutically acceptable carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds of the present invention, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-$\beta$-aminopropionates, and 2-alkyl-imidazoline quaternary ammonium salts, and (e) mixtures thereof.

The parenteral formulations will typically contain from about 0.5% to about 25% by weight of the compound of the present invention or a salt, solvate or stereoisomer thereof, in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compound of the present invention, or a salt, solvate, stereoisomer, or prodrug thereof, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compound of the present invention, or a salt, solvate, stereoisomer, or prodrug thereof, also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 10 mg/kg body weight/day, and from about 0.1 mg to about 1 mg/kg body weight/day.

Alternatively, the compounds of the present invention, or a salt, solvate, stereoisomer, or prodrug thereof, can be modified into a depot form, such that the manner in which the compound is released into the body to which it is administered is controlled with respect to time and location within the body (see, for example, U.S. Pat. No. 4,450,150). Depot forms of compound can be, for example, an implantable composition comprising the compound and a porous or non-porous material, such as a polymer, wherein compound is encapsulated by or diffused throughout the material and/or degradation of the non-porous material. The depot is then implanted into the desired location within the body and the compounds are released from the implant at a predetermined rate.

In one embodiment, the compounds of the present invention, or salts, solvates or stereoisomers thereof, provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially all of the RNase H inhibitor is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds of the present invention, or salts, solvates or stereoisomers thereof, may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compounds may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

EXAMPLES

Unless otherwise stated, all reactions were carried out under an atmosphere of dry argon or nitrogen in dried glassware. Indicated reaction temperatures refer to those of the reaction bath, while room temperature (rt) is noted as about 25° C. All solvents were of anhydrous quality purchased from Aldrich Chemical Co. (St. Louis, Mo.) and used as received. Commercially available starting materials and reagents were purchased from Aldrich and were used as received.

Synthesis of compounds: All air or moisture sensitive reactions were performed under positive pressure of nitrogen with oven-dried glassware. Anhydrous solvents such as tetrahydrofuran (THF), toluene, dichloromethane, N,N-dimethylformamide (DMF), acetonitrile, methanol and triethylamine were obtained by purchasing from Sigma-Aldrich. Purification of the compounds was performed on Waters UPLC or Biotage SP systems. Samples were analyzed for purity on an Agilent 1200 series LC/MS equipped with a Zorbax™ Eclipse XDB-C18 reverse phase (5 micron, 4.6×150 mm) column having a flow rate of 0.8 ml/min (Agilent Technologies, Santa Clara, Calif.). The mobile phase was a mixture of acetonitrile and $H_2O$ each containing 0.05% trifluoroacetic acid. Gradient of 4% to 100% acetonitrile (0.05% TFA) over 7 minutes with flow rate of 0.8 ml/min using Luna C18 3 micron 3×75 mm column (Phenomenex, Inc., Torrance, Calif.). All of the analogues used for assay have purity greater than 95%. High resolution mass spectrometry was recorded on Agilent 6210 Time-of-Flight LC/MS system. All of the final analogues are the mixture of diastereomers which are inseparable on preparative HPLC.

The synthesis of manicol epoxide is based on the following reference: Polonsky, J. *Tetrahedron*, 39:2647-2655 (1983). A schematic of the reaction is provided below.

Scheme 1. The synthesis of manicol epoxide

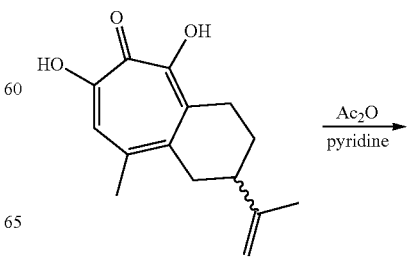

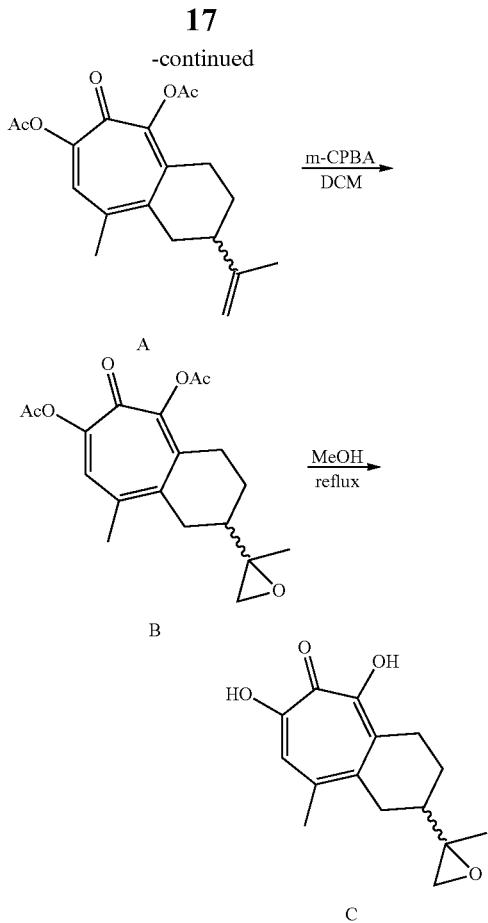

Example 1

Synthesis of 5,7-Dihydroxy-2-(1-hydroxy-1-methyl-2-piperidin-1-yl-ethyl)-9-methyl-1,2,3,4-tetrahydro benzocyclohepten-6-one (Compound 1). To a solution of manicol epoxide (compound C) (7 mg, 0.027 mmol) in acetonitrile (0.5 ml) was added piperidine (18.2 mg, 0.213 mmol, 8.0 eq.) and lithium perchlorate (5.7 mg, 0.053 mmol, 2 eq.). The mixture was refluxed for 1 hour. After cooling to room temperature, another 1.5 ml acetonitrile was added and the mixture was directly subject to preparative HPLC purification to give the desired product Compound 1 as a brownish solid (4 mg, 54%). $^1$H NMR (400 MHz, DMSO-$d_6$) δ 8.83-8.58 (br.s., 1H), 7.37 (s, 1H), 5.75 (s, 1H), 5.55-5.23 (br.s., 1H), 3.62-3.40 (m, 2H), 3.29-3.17 (m, 2H), 3.13-2.96 (m, 3H), 2.92-2.67 (m, 2H), 2.59-2.50 (m, 3H), 2.41 (s, 3H), 2.05-1.85 (m, 1H), 1.85-1.68 (m, 4H), 1.67-1.57 (m, 1H), 1.52-1.37 (m, 1H), 1.29 and 1.25 (s, 3H); LC/MS: Retention time: 3.449 minutes; HRMS: m/z (M+H$^+$)=348.2176 (Calculated for $C_{20}H_{30}NO_4S$=348.2175).

Example 2

Synthesis of 5,7-Dihydroxy-2-(1-hydroxy-2-imadazol-1-yl-1-methyl-ethyl)-9-methyl-1,2,3,4-tetrahydro benzocyclohepten-6-one (Compound 2). Compound 2 was prepared in the same manner as Compound 1, except for using imidazole as a nucleophile. $^1$H NMR (400 MHz, DMSO-$d_6$) δ 9.03 and 9.01 (s, 1H), 7.72-7.64 (m, 2H), 7.38 and 7.36 (s, 1H), 5.25-5.03 (br.s., 1H), 4.36-4.21 (m, 2H), 3.80-3.30 (br.s., 2H), 3.20-3.00 (m, 1H), 3.00-2.60 (m, 2H), 2.44 and 2.40 (s, 3H), 2.62-2.47 (m, 1H), 2.25-1.92 (m, 1H), 1.75-1.48 (m, 1H), 1.45-1.25 (m, 1H), 1.01 and 1.00 (s, 3H); LC/MS: Retention time: 3.337 minutes; HRMS: m/z (M+H$^+$)=331.1651 (Calculated for $C_{18}H_{23}N_2O_4$=331.1658).

Example 3

Synthesis of 2-(2-Diethylamino-1-hydroxy-1-methyl-ethyl)-5,7-dihydroxy-9-methyl-1,2,3,4-tetrahydrobenzocyclohepten-6-one (Compound 3) was prepared in the same manner as Compound 1 except for using diethylamine as a nucleophile. $^1$H NMR (400 MHz, DMSO-$d_6$) δ 8.56-8.33 (br.s., 2H), 7.38 and 7.37 (s, 1H), 5.50-5.28 (br.s., 1H), 3.95-3.35 (m, 4H), 3.34-3.10 (m, 4H), 3.10-2.90 (m, 1H), 2.87-2.55 (m, 1H), 2.54 and 2.52 (s, 3H), 2.25-1.85 (m, 1H), 1.75-1.58 (m, 1H), 1.35-1.15 (m, 10H); LC/MS: Retention time: 3.427 minutes; HRMS: m/z (M+H$^+$)=336.2171 (Calculated for $C_{19}H_{30}NO_4$=336.2175).

Example 4

Synthesis of 2-[2-(2-Fluoro-benzylamino)-1-hydroxy-1-methyl-ethyl]-5,7-dihydroxy-9-methyl-1,2,3,4-tetrahydrobenzocyclohepten-6-one (Compound 4). Compound 4 was prepared in the same manner as Compound 1, except for using 2-fluoroaniline as a nucleophile. $^1$H NMR (400 MHz, DMSO-$d_6$) δ 8.90-8.60 (br.s., 2H), 7.70-7.61 (m, 1H), 7.54-7.45 (m, 1H), 7.36 and 7.35 (s, 1H), 7.34-7.35 (m, 2H), 5.48-5.15 (br.s., 1H), 4.25 (s, 2H), 3.20-2.90 (m, 3H), 2.90-2.61 (m, 2H), 2.38 and 2.34 (s, 3H), 2.50-2.35 (m, 2H), 2.15-1.92 (m, 1H), 1.80-1.65 (m, 1H), 1.33-1.13 (m, 1H), 1.20 and 1.18 (s, 3H); LC/MS: Retention time: 3.844 minutes; HRMS: m/z (M+H$^+$)=388.1914 (Calculated for $C_{22}H_{27}FNO_4$=388.1924).

Example 5

Synthesis of 5,7-Dihydroxy-2-(1-hydroxy-1-methyl-2-phenylamino-ethyl)-9-methyl-1,2,3,4-tetrahydrobenzocyclohepten-6-one (Compound 5). Compound 5 was prepared in the same manner as Compound 1 except for using aniline as a nucleophile. $^1$H NMR (400 MHz, CDCl$_3$) δ 7.50 and 7.49 (s, 1H), 7.34-7.25 (m, 2H), 7.05-6.94 (m, 3H), 3.43-3.17 (m, 2H), 3.04-2.82 (m, 2H), 2.64-2.33 (m, 2H), 2.48 and 2.46 (s, 3H), 2.23-2.03 (m, 1H), 2.02-1.84 (m, 2H), 1.53-1.39 (m, 1H), 1.38 and 1.31 (s, 3H). LC/MS: Retention time min: 4.715 minutes; HRMS: m/z (M+H$^+$)=356.1864 (Calculated for $C_{21}H_{26}NO_4$=356.1862).

Example 6

Synthesis of 2-(2-Ethylthio-1-hydroxy-1-methyl-ethyl)-5,7-dihydroxy-9-methyl-1,2,3,4-tetrahydrobenzocyclohepten-6-one (Compound 6). Compound 6 was prepared in the same manner as Compound 5 except for using ethanethiol as a nucleophile. $^1$H NMR (400 MHz, CDCl$_3$) δ 7.49 and 7.48 (s, 1H), 3.28-3.24 and 3.24-3.19 (m, 1H), 3.03-2.78 (m, 2H), 2.76-2.64 (m, 2H), 2.60-2.50 (m, 1H), 2.48 and 2.47 (s, 3H), 2.16-2.02 (m, 2H), 1.83-1.71 (m, 1H), 1.70-1.59 (m, 1H), 1.56-1.25 (m, 4H), 1.40 and 1.38 (s, 3H); LC/MS: Retention time: 5.529 minutes; HRMS: m/z (M+H$^+$)=325.1466 (Calculated for $C_{17}H_{25}O_4S$=325.1474).

Example 7

Synthesis of 5,7-Dihydroxy-2-(1-hydroxy-1-methyl-2-phenylthio-ethyl)-9-methyl-1,2,3,4-tetrahydrobenzocyclohepten-6-one (Compound 7). To a solution of manicol epoxide (compound C) (15 mg, 0.057 mmol) in THF (1 ml) was added thiophenol (0.20 ml, 1.94 mmol, 34 eq.) and Et$_3$N (0.08 ml, 0.57 mmol, 10 eq.), and the solution was refluxed overnight. After cooling to room temperature, the mixture was directly purified by HPLC to give the desired product (Compound 7) as a light yellow solid (10 mg, 47%). $^1$H NMR (400 MHz, CDCl$_3$) δ 7.50 and 7.49 (s, 1H), 7.46-7.39 (m, 2H), 7.33-7.18 (m, 3H), 3.37-3.10 (m, 3H), 3.05-2.91 (m, 1H), 2.91-2.76 (m, 1H), 2.67-2.50 (m, 2H), 2.48 and 2.42 (s, 3H), 1.98-1.85 (m, 1H), 1.49-1.33 (m, 1H), 1.32 and 1.26 (s, 3H); LC/MS: Retention time: 6.101 minutes; HRMS: m/z (M+H$^+$)=373.1472 (Calculated for C$_{21}$H$_{25}$O$_4$S=373.1474).

Example 8

Synthesis of 2-(2-Benzylthio-1-hydroxy-1-methyl-ethyl)-5,7-dihydroxy-9-methyl-1,2,3,4-tetrahydrobenzocyclohepten-6-one (Compound 8). To a solution of BnSH (26 mg, 0.21 mmol) in MeOH (1 ml) was added NaH (4.6 mg, 0.19 mmol) and the mixture was stirred for 10 min. Manicol epoxide (compound C) (5 mg, 0.019 mmol) was added and the mixture was stirred overnight at room temperature and directly purified by preparative HPLC to give the desired product (Compound 8) (3 mg, 58%): $^1$H NMR (400 MHz, DMSO-d$_6$) 7.35 and 7.34 (s, 1H), 7.33-7.28 (m, 4H), 7.25-7.20 (m, 1H), 3.79-3.76 (m, 2H), 3.06-2.94 (m, 1H), 2.82-2.60 (m, 5H), 2.48-2.36 (m, 1H), 2.34 and 2.33 (s, 3H), 1.30-1.16 (m, 2H), 1.15 and 1.13 (s, 3H); Retention time: 6.157 minutes; HRMS: m/z (M+H$^+$)=387.1620 (Calculated for C$_{22}$H$_{27}$O$_4$S=387.1630).

Example 9

Synthesis of 2-(2-Ethanesulfonyl-1-hydroxy-1-methyl-ethyl)-5,7-dihydroxy-9-methyl-1,2,3,4-tetrahydrobenzocyclohepten-6-one (Compound 9). Compound 9 was prepared through oxidation of corresponding sulfide Compound 6 with m-CPBA in CH$_2$Cl$_2$ at room temperature. $^1$H NMR (400 MHz, DMSO-d$_6$) δ 7.36 and 7.35 (s, 1H), 3.42-3.26 (m, 2H), 3.11-2.98 (m, 1H), 2.89-2.67 (m, 2H), 2.60-2.45 (m, 4H), 2.40 and 2.39 (s, 3H), 2.02-1.79 (m, 1H), 1.77-1.65 (m, 1H), 1.45-1.12 (m, 3H), 1.07 and 1.05 (s, 3H); LC/MS: Retention time: 4.323 minutes; HRMS: m/z (M+H$^+$)=357.1370 (Calculated for C$_{17}$H$_{25}$O$_6$S=357.1372).

Example 10

Synthesis of 2-(2-Benzylsulfinyl-1-hydroxy-1-methyl-ethyl)-5,7-dihydroxy-9-methyl-1,2,3,4-tetrahydrobenzocyclohepten-6-one (Compound 10). Compound 10 was prepared by oxidation of corresponding the sulfide with m-CPBA at −78° C., while 2-(2-benzenesulfonyl-1-hydroxy-1-methyl-ethyl)-5,7-dihydroxy-9-methyl-1,2,3,4-tetrahydrobenzocyclohepten-6-one (Compound 11) was prepared by oxidation using m-CPBA at room temperature. Compound 10: $^1$H NMR (400 MHz, DMSO-d$_6$) δ 7.72-7.66 (m, 2H), 7.63-7.52 (m, 3H), 7.37 and 7.36 (s, 1H), 3.23-2.80 (m, 4H), 2.62-2.50 (m, 2H), 2.42 and 2.41 (s, 3H), 2.15-1.90 (m, 3H), 1.40-1.15 (m, 4H); LC/MS: Retention time: 4.767 minutes; HRMS: m/z (M+H$^+$)=389.1422 (Calculated for C$_{21}$H$_{25}$O$_5$S=389.1423). Compound 11: $^1$H NMR (400 MHz, DMSO-d$_6$) δ 10.61 (s, 1H), 9.98 (s, 1H), 7.96-7.87 (m, 2H), 7.74-7.66 (m, 1H), 7.75-7.58 (m, 2H), 7.45-7.38 (m, 2H), 4.10-3.50 (m, 3H), 2.64-2.54 (m, 2H), 2.53 and 2.52 (s, 3H), 2.34-2.18 (m, 2H), 2.17-1.94 (m, 1H), 1.94-1.76 (m, 1H), 1.43-1.28 (m, 1H), 1.24 and 1.23 (s, 3H). LC/MS Retention time: 5.123 minutes; HRMS: m/z (M+H$^+$)=405.1354 (Calculated for C$_{21}$H$_{25}$O$_6$S=405.1360).

Example 11

Synthesis of 2-(1,2-Dihydroxy-1-methyl-ethyl)-5,7-dihydroxy-9-methyl-1,2,3,4-tetrahydrobenzocyclohepten-6-one (Compound 12). To a solution of diacetate (Compound C) (5 mg, 0.014 mmol) in acetone/H$_2$O (0.19 ml/0.02 ml) was added 2.5 wt % tert-BuOH OsO$_4$ solution (7.7 µl, 0.757 µmol) and N-methylmorpholine oxide (3.4 mg, 0.029 mmol) and the mixture was stirred for 3 hours. EtOAc (10 ml) was added and the solution was washed with 10% aqueous Na$_2$SO$_3$ solution and brine. The organic layer was dried over MgSO$_4$. After the removal of EtOAc, the crude product was redissolved in MeOH (2 ml) and the refluxed for 5 hours. The solution was concentrated to 2 ml and directly subject to preparative HPLC purification to give the desired diol (Compound 12) (3 mg, 71%). $^1$H NMR (400 MHz, DMSO-d$_6$) δ 7.36 and 7.35 (s, 1H), 3.42-3.27 (m, 2H), 3.11-2.97 (m, 1H), 2.89-2.65 (m, 2H), 2.58-2.44 (m, 1H), 2.39 and 2.38 (s, 3H), 2.00-1.81 (m, 1H), 1.76-1.64 (m, 1H), 1.36-1.20 (m, 2H), 1.06 and 1.05 (s, 3H); LC/MS: Retention time: 3.795 minutes; HRMS: m/z (M+H$^+$)=281.1386 (Calculated for C$_{15}$H$_{21}$O$_5$=281.1389).

Example 12

Synthesis of 5,7-Dihydroxy-2-(1-hydroxy-ethyl)-9-methyl-1,2,3,4-tetrahydrobenzocyclohepten-6-one (Compound 13). To a solution of (Compound A) (22 mg, 0.07 mmol) in tert-BuOH/H$_2$O (1.8 ml/0.36 ml) was added 2.5 wt % tert-BuOH OsO$_4$ solution (0.42 ml, 0.042 mmol), NaIO$_4$ (123 mg, 0.58 mmol) and NaHCO$_3$ (81 mg, 0.96 mmol) and the mixture was stirred for 2 hours at room temperature. 10% Na$_2$SO$_3$ (1.5 ml) was added and the mixture was stirred for 0.5 hours and extracted with CH$_2$Cl$_2$ (3×10 ml), and the combined organic layers were washed with brine and dried over Na$_2$SO$_4$. After the removal of organic solvent, the residue was purified by column chromatography (EtOAc/Hexane 1/1) to give the desired ketone 5,7-Diaceto-2-(1-keto-ethyl)-9-methyl-1,2,3,4-tetrahydrobenzocyclohepten-6-one (Compound 17) (20 mg, 90%). Compound 17 was then dissolved in MeOH (2 ml) and NaBH$_4$ (6 mg, 0.16 mmol) was added and stirred at room temperature for 0.5 hours. After the complete reduction of the ketone monitored by LC/MS, the mixture was further refluxed for 5 hours and directly purified by preparative HPLC to give Compound 13. $^1$H NMR (400 MHz, CDCl$_3$) δ 7.51 and 7.50 (s, 1H), 3.84-3.77 and 3.76-3.63 (m, 1H), 3.29-3.18 (m, 1H), 3.05-2.94 (m, 2H), 2.84 and 2.79 (d, J=3.9 Hz, 1H), 2.70-2.51 (m, 1H), 2.51 and 2.48 (s, 3H), 2.16-2.06 and 2.03-1.93 (m, 1H), 1.78-1.66 (m, 1H), 1.49-1.34 (m, 1H), 1.31 (d, J=6.3 Hz, 3H); LC/MS: Retention time: 4.315 minutes; HRMS: m/z (M+H$^+$)=251.1280 (Calculated for C$_{14}$H$_{19}$O$_4$=251.1283).

Example 13

Synthesis of 2-(1-Benzylamino-ethyl)-5,7-Dihydroxy-9-methyl-1,2,3,4-tetrahydrobenzocyclohepten-6-one (Compound 14). To a solution of (Compound 17) (5 mg, 0.015 mmol) in 1,2-dichloroethane (0.1 ml) was added benzylamine (1.6 µl, 0.016 mmol) and sodium triacetoxyborohydride (4.5 mg, 0.021 mmol) and the mixture was stirred overnight at room temperature. LC/MS indicated the formation of de-acetylated product (Compound 14). The mixture was directly purified by preparative HPLC to give desired product (Compound 14) (3 mg, 59%). $^1$H NMR (400 MHz, DMSO-d$_6$) δ 9.03-8.85 (br.s., 1H), 8.73-8.56 (br.s., 1H), 7.63-7.51 (m, 2H), 7.51-7.40 (m, 3H), 7.37 (s, 1H), 4.37-4.14 (m, 2H), 3.45-3.27 (m, 1H), 3.20-3.00 (m, 1H), 2.97-2.63 (m, 2H), 2.58-2.44 (m, 2H), 2.39 and 2.37 (s, 3H), 2.25-2.05 (m, 1H), 2.03-1.93 and 1.92-1.83 (m, 1H), 1.42-1.28 (m, 4H). LC/MS: Retention time: 3.913 minutes; HRMS: m/z (M+H$^+$) =340.1908 (Calculated for C$_{21}$H$_{26}$NO$_3$=340.1913).

Example 14

This Example describes HIV-1 RT expression and purification for use in biochemical analysis.

(His)$_6$-tagged p66/p51 HIV-1$_{HXB2}$ RT, the single subunit XMRV$_{VP62}$ RT and RNase H-deficient mutants were expressed from recombinant *Escherichia coli* and purified by a combination of immobilized metal affinity and ion exchange chromatography as previously described (LeGrice, S. F., et al., *Eur. J. Biochem.*, 187(2):307-14 (1990). Purified enzymes were stored at −20° C. in a buffer of 50 mM Tris/HCl, pH 7.0, 25 mM NaCl, 1 mM EDTA, 1 mM dithiothreitol and 50% (v/v) glycerol.

Example 15

The following example illustrates the RNase H Inhibitor activity against HIV for the described compounds in accordance with an embodiment of the present invention.

IC$_{50}$ values were determined as previously reported (Budihas, S. R., et al., *Nucleic Acids Res.*, 33(4):1249-56 (2005)), using an 18-nucleotide 3'-flourescein-labeled RNA annealed to a complementary 18-nucleotide 5'-dabsyl-labeled DNA. Cleavage of the HIV-1 polypurine tract (PPT) primer was performed with a 29 nt Cy5-labeled RNA (5'-Cy5-UUU UAA AAG AAA AGG GGG G*AC UGG AAG GG-3' (SEQ ID NO: 1), where * represents the PPT 3' terminus hybridized to a 40 nt DNA (5'-ATT AGC CCT TCC AGT CCC CCC TTT TCT TTT AAA AAG TGG C-3' (SEQ ID NO: 2); XMRV PPT: 5'-Cy5-UUU CCA GAA AGA GGG GGG AAU GAA AGA C-3' (SEQ ID NO: 3), 5'-GTG GGG TCT TTC ATT CCC CCC TCT TTC TGG AAA CTG AAT A-3' (SEQ ID NO: 4); HIV-1 Non-PPT: 5'-Cy5-UCA UGC CCU GCU AGC UAC UCG AUA UGG CAA UAA GAC UCC A-3' (SEQ ID NO: 5); 5'-TGG AGT CTT ATT GCC ATA TCG AGT AGC TAG-3' (SEQ ID NO: 6)). The reaction was initiated by adding 1 µl of 100 mM MgCl$_2$ to 9 µl of mixture containing 4 ng enzyme, 200 nM substrate, 20 µM α-hydroxytropolones in 50 mM Tris, pH 8.0, 80 mM KCl, 2 mM DTT, and 10% DMSO at 37° C., and quenched with 10 µl of a gel-loading buffer after 10 minutes. Hydrolysis products were fractionated by denaturing polyacrylamide gel electrophoresis and visualized by fluorescent imaging (Typhoon Trio+, GE Healthcare, Piscataway, N.J.).

Example 16

The following example illustrates the DNA polymerase assays used with the described compounds in accordance with an embodiment of the present invention.

DNA-dependent DNA synthesis was measured on a fluorescently-labeled duplex DNA prepared by annealing a 33-nt template, 5'-CAC TGC TCA AGA AGT TCC AAT CCT AAA TAC ATA-3' (SEQ ID NO: 3), to the 5'-Cy5-labeled primer 5'-ATG TAT GGG TAT GTA TTT AGG-3' (SEQ ID NO: 4). Polymerization was initiated by adding 1 µl of 2 mM dNTPs to 9 µl of mixture containing 4 ng enzyme, 200 nM substrate, 20 µM α-hydroxytropolones in 10 mM Tris, pH 7.8, 80 mM KCl, 1 mM DTT, 10 mM MgCl$_2$, and 10% DMSO at 37° C.

DNA synthesis was quenched with 10 µl of a gel-loading buffer after 10 minutes, and reaction products were analyzed by denaturing polyacrylamide gel electrophoresis and fluorescent imaging.

Example 17

The following example illustrates the HIV-1 cytopathicity assay used with the described compounds in accordance with an embodiment of the present invention.

This assay was conducted as previously reported (Weislow, O, S., et al., *J. Natl. Cancer Inst.*, 81(8):577-86 (1989)). Samples were dissolved in DMSO at 10 mM and diluted to a final high concentration of 50 µM in the 96-well assay plate, with 2-fold dilutions made to a low concentration of about 0.78 µM. All samples were tested in duplicate. The HIV-1 virus strain RF was used to infect CEM-SS cells. Compound cytotoxicity was measured in the same assay plate using uninfected cells. Regression analysis was used to estimate the effective concentration (EC$_{50}$) as well as the cytotoxic concentration (CC$_{50}$).

Example 18

The following example illustrates the expression and purification of HIV-1 RT for structural studies used with the described compounds in accordance with an embodiment of the present invention.

An HIV-1 RT variant designated RT52A was used for X-ray diffraction studies. In this variant, which was optimized for crystallization of RT with nucleoside or non-nucleoside RT inhibitors (NRTIs and NNRTIs, respectively), the p66 subunit was truncated at residue 555. The p51 subunit contained a HRV14-3C protease cleavable N-terminal hexa-histidine tag, and was truncated at residue 428. Both subunits contained the mutation C280S. The p66 subunit also contained the mutations K172A and K173A. RT52A was then expressed and purified as previously described (Bauman, J. D., et al., *Nucleic Acids Res.*, 36(15):5083-5092 (2008)). Briefly, 1 mM isopropyl β-D-1-thiogalactopyranoside (IPTG) was used to induce BL21-CodonPlus®-RIL (Stratagene, Santa Clara, Calif.) containing a plasmid encoding both subunits of RT69A at an OD600 of 0.9 and the culture was incubated for three hours at 37° C. The cells were pelleted and lysed by sonication. Protein was purified by Ni-NTA according to manufacturers' recommendations (Qiagen, Valencia, Calif.) with the following modifications: each buffer contained 600 mM NaCl, no lysozyme was added, and a 1.2 M NaCl wash was added. Eluted protein was incubated with HRV14-3C protease overnight at 4° C. A Mono Q purification step (GE Healthcare, Piscataway, N.J.) was performed as described (Clark-Jr., A. D., et al., *Methods in Enzymology: Macromolecular Crystallography Part A.*, J. Charles W. Carter and R. M. Sweet, Eds. 1997, Academic Press, Inc.: New York. p. 307-326).

Example 19

The following example illustrates the crystallization and data collection methods used with the described compounds in accordance with an embodiment of the present invention.

HIV-1 RT52A was co-crystallized with manicol and TMC278 (rilpilvirine) at 4° C., by vapor diffusion in micro-seeded hanging drops containing 1.2 µl each of 20 mg/ml protein (in a solution of 9.2 mM Tris pH 8.0, 68.7 mM NaCl, 3.6 mM manganese sulfate, 0.7 mM tris(2-carboxyethyl) phosphine (TCEP), 0.27% β-octyl glucopyranoside, 7% dimethyl sulfoxide, 0.9 mM manicol, and 0.7 mM TMC278, pre-incubated for 30 minutes on ice) and a reservoir solution containing 50 mM HEPES pH 7.5, 100 mM ammonium sulfate, 15 mM manganese sulfate, 10 mM spermine, 5 mM TCEP, and 11% PEG 8000. The chosen crystal was soaked for 120 seconds in a solution containing 50 mM HEPES pH 7.5, 50 mM NaCl, 100 mM ammonium sulfate, 15 mM manganese sulfate, 10 mM spermine, 15% PEG 8000, 5% PEG 400, 10% DMSO, 11% ethylene glycol, 6.5% trimethylamine-N-oxide (TMAO), 0.69 mM manicol, and 0.34 mM TMC278. The crystal was subsequently flash-cooled and stored in liquid $N_2$. X-ray data were collected at 100K and a wavelength of 1.1 Å at the National Synchrotron Light Source at Brookhaven National Laboratories, Beamline X25. The data were processed using the HKL-DENZO/SCALEPACK software suite (Otwinowski, Z. and W. Minor, *DENZO and SCALEPACK*, in *International Tables for Crystallography Volume F: Crystallography of Biological Macromolecules*, M. G. Rossmann and E. Arnold, Eds. 2001, Kluwer Academic Publishers: Boston. p. 226-235; Otwinowski, Z. and W. Minor, *Processing of X-Ray Diffraction Data Collected in Oscillation Mode*, in *Methods in Enzymology: Macromolecular Crystallography Part A.*, J. Charles W. Carter and R. M. Sweet, Eds. 1997, Academic Press, Inc.: New York. p. 307-326).

Example 20

The following example depicts the structure determination methods used with the described compounds in accordance with an embodiment of the present invention.

Phases for the diffraction data were determined by molecular replacement with the CCP4 program PHASER (Read, R. J., *Acta Crystallogr. D Biol. Crystallogr.*, 57:1373-1382 (2001)), using an RT/TMC278 structure (PDB accession number 2ZD1) (Das, K., et al., *Proc. Natl. Acad. Sci. USA*, (5):1466-1471 (2008)) as an initial search model. Stepwise model building and refinement were conducted using the "O" graphics package (Jones, T. A., et al., *Acta. Crystallogr. A.*, 47:110-119 (1991)), the Coot graphics package (Emsley, P. and K. Cowtan, *Acta Crystallogr. D Biol. Crystallogr.*, 60(Pt 12, Pt 1):2126-2132 (2004)), and CNS (Brünger, A. T., et al., *Acta Crystallogr. D Biol. Crystallogr.*, 54(Pt 5):905-921 (1998)) with a bulk solvent correction (Table 1). Water molecules were built in using the program Refmac/ARP/wARP in the CCP4 software suite (See, for example, Lamzin, V. S., et al., *The ARP/wARP Suite for Automated Construction and Refinement of Protein Models*, in *International Tables for Crystallography Volume F: Crystallography of Biological Macromolecules*, M. G. Rossmann and E. Arnold, Eds. 2001, Kluwer Academic Publishers: London. pp. 720-722). The geometry of the inhibitor and refinement of the RNH active site were improved by energy minimization using the Impact and PrimeX facilities of the Schrödinger software package (Schrödinger, LLC, New York, N.Y.).

TABLE 1

Data collection and refinement statistics for p66/p51 HIV-1 RT/TMC278/manicol cocrystal.

PDB ID:

| (a) Unit Cell Parameters (Space Group C2)* | |
|---|---|
| a (Å): | 163.2 |
| b (Å): | 73.0 |
| c (Å): | 108.4 |
| γ (Å): | 101.1 |
| (b) Data Collection | |
| Resolution Range: | 45-2.7 Å |
| $R_{sym}$(%): | 6.3 |
| Average I/σ | 16.1 |
| Completeness (%): | 99.5 |
| Unique Reflections/Multiplicity: | 34841/6.2 |
| (c) Refinement | |
| Sigma Cutoff: | 0.0 |
| Resolution Range Used (Å): | 45-2.7 |
| Completeness of Used Reflections (%): | 95.8 |
| R-factor/$R_{free}$(%): | 23.2/25.8 |
| Cross-Validated Coordinate Error (Å): | |
| No. of Protein/Solvent Atoms: | 7930/69 |
| No. of Ligand/Cation Atoms: | 49/2 |
| Average B-Factors (Å$^2$): | |
| Protein/Solvent: | 78.0/53.2 |
| Ligands/Cations: | 77.8/69.7 |
| RMS Bond Lengths (Å)/Angles (°): | 0.009/1.52 |
| (d) Ramachandran Regions | |
| Most Favored: | 95.8 |
| Additional Allowed: | 4.2% |
| Generous or Disallowed: | 0% |

Example 21

The following example depicts the structures of HIV-1 RT containing manicol and the NNRI TMC278, as well as the methods used with the described compounds, in accordance with an embodiment of the present invention.

α-hydroxytropolone, the related natural product of manicol is more readily amenable to derivatization. In order to guide the synthesis of the compounds of the present invention, the structure of p66/p51 HIV-1 RT containing the non-nucleoside inhibitor (NNI) TMC278, in the DNA polymerase domain, and manicol at the RNase H active site was solved. The structure, refined at 2.7 Å resolution (Table 1), revealed unambiguous electron density maps for manicol binding (data not shown). Two strong $Mn^{2+}$ peaks in the electron density map within the RNase H active site correspond to the divalent cation positions "A" and "B" (following the convention for a two-cation mechanism of hydrolysis. The carbonyl oxygen and both hydroxyls of the tropolone ring coordinate the divalent cations in a manner similar to that previously observed in the RT/β-thujaplicinol structure.

However, unlike β-thujaplicinol, manicol forms extensive contacts with the imidazole ring of His539, including one atomic contact with an interatomic distance of just under 3 Å (data not shown). The electron density indicates that the alicyclic carbon atoms of manicol pucker in the direction of the His539 side-chain, with the 2-isopropenyl substituent occupying the equatorial position on the $C_{10}$ carbon. This observation is in contrast to a previous small molecule crystal structure study of Polonsky et al. where the 2-isopropenyl substituent possessed an axial orientation (Polonsky, J., et al., *Tetrahedron*, 39(16):2647-2655 (1983)). In both the present invention and the Polonsky et al. study, the chiral center at the $C_{10}$ carbon has an S configuration. While in the RT/β-thujaplicinol structure, one hydroxyl group of the tropolone ring came within hydrogen bonding distance of the side-chain carboxylates of the catalytically-critical residues Glu478 and Asp498, significantly, it was presently found that manicol pivots away from these residues and loses these interactions in favor of contacts with His539 and a 2.3 Å contact between one of the tropolone hydroxyls and the side-chain carboxylate of Asp549.

Example 22

The following example depicts the synthetic methods used to prepare the described compounds in accordance with embodiments of the present invention.

The general synthesis of the compounds in accordance with embodiments of the present invention is depicted in FIG. 1. Manicol epoxide (Compound 16) was synthesized according to Polonsky, J. supra. Opening of the epoxide with a variety of amines catalyzed by stoichiometric $LiClO_4$ afforded Compounds 1-5. Addition of selected thiols required $Et_3N$ or NaH and resulted in the sulfide derivatives of Compounds 6-8. Compounds 6 and 7 were oxidized with m-CPBA to either a sulfoxide (Compound 10) or sulfones (Compounds 9, 11) by adjusting the reaction temperature. Starting from diacetyl protected manicol intermediate (Compound 15), dihydroxylation of olefin functionality using $OsO_4$/NMO followed by the deprotection of the acetyl groups gave Compound 12. Alternatively, in the presence of $OsO_4$ and $NaIO_4$, the in situ dihydroxylation/oxidative cleavage of Compound 15 resulted in a ketone derivative (Compound 17), which could be reduced to an alcohol (Compound 13) with $NaBH_4$, or converted to amine (Compound 14) via reductive amination. It should be noted all of the tested analogues (Compounds 1-14) were obtained as a mixture of diastereomers.

Example 23

The following example depicts the in vitro methods of inhibition of RNase H activity used with the described compounds in accordance with embodiments of the present invention.

Using a sequence-independent RNA/DNA hybrid and our previously reported high throughput RNase H assay (Parniak, M. A., et al., *Anal. Biochem.*, 322(1):33-39 (2003)), Table 2 illustrates the $IC_{50}$ values for Compounds 1-14. Compound 9 was slightly more potent than manicol ($IC_{50}$ 0.26 µM vs 0.6 µM, respectively), while a 3-4-fold decrease in activity was observed for Compound 2 ($IC_{50}$ 2.10 µM). All remaining compounds fell within this range. Since the high-throughput RNase H assay examines non-specific, "polymerase-independent" RNase H activity defined by the spatial separation of the DNA polymerase and RNase H active site of HIV-1 RT (Gopalakrishnan, V., et al., *Proc. Natl. Acad. Sci. USA*, 89(22):10763-7 (1992)), an examination of whether α-hydroxytropolones altered cleavage specificity on a more biologically-relevant substrate, namely the polypurine tract (PPT) primer, which must be processed from the RNA/DNA replication intermediate to initiate (+) strand DNA synthesis. In this experiment, Compounds 1-14 were assayed at a final concentration of 20 µM.

In all instances, primary RNase H-mediated hydrolysis occurred at the 5'-pG< >pA-3' PPT/U3 junction, with additional cleavage at the immediately adjacent 5'-pG-pG-3' sequences. Thus, while differing levels of inhibition were observed with compounds 1-14, in the PPT assay none altered cleavage specificity. In keeping with the data of Table 2, Compound 9 was almost 100% effective in inhibiting PPT/U3 cleavage, while Compounds 2, 4, 10, and 14 were less active. Interestingly, some inhibitors, e.g., Compounds 3 and 11, were ineffective in inhibiting PPT/U3 cleavage, while being more active on the non-specific RNA/DNA hybrid. In contrast, Compound 5 was more active in blocking PPT/U3 cleavage than inhibiting polymerase-dependent cleavage on the non-specific substrate. The data of Table 2 thus illustrates potential benefits of including model systems that mimic some of the more complex RNase H-mediated events in HIV replication as screening tools.

Example 24

The following example depicts the in vitro methods for inhibition of DNA polymerase activity by the described compounds in accordance with embodiments of the present invention.

In order to examine the specificity of our manicol analogs, their effect on the DNA polymerase activity of wild type p66/p51 HIV-1 RT and RNase H-deficient derivatives was determined. In particular, RNase H-deficient strains $p66^{EQ}$/p51 and $p66^{D4}$/p51, were tested, which harbor mutations in one of the catalytically-critical amino acids contacted by manicol (E478 and D549, respectively), that would be predicted to interfere with α-hydroxytropolone binding.

The results of the analysis are presented in FIG. 3. In general, manicol analogs had minimal effect on DNA polymerase activity of RNase H-deficient $p66^{EQ}$/p51 and $p66^{D4}$/p51 RT, suggesting specificity for the RNase H active site. However, two exceptions were noted, namely compounds 5 and 10, which significantly and consistently inhibited DNA-dependent DNA polymerase activity of both mutants. Although crystallographic evidence is presently unavailable, compounds 5 and 10, thus appear capable of occupying a second site on HIV-1 RT.

TABLE 2

In Vitro Inhibition of RNase H Activity and Inhibition of HIV Cytopathicity

| Inhibitor | In vitro $IC_{50}$ (µM) | Virus Replication $EC_{50}$ (µM) | $CC_{50}$ (µM) |
|---|---|---|---|
| β-Thujaplicinol | 0.21 | n.p. | 2.3 |
| Manicol | 0.60 | n.p. | 13.6 |
| 1 | 0.93 | 10.2 | >50 |
| 2 | 2.10 | 42.1 | >50 |
| 3 | 0.49 | <50% | >50 |
| 4 | 1.40 | n.p. | >50 |
| 5 | 1.20 | 7.4 | 31.7 |
| 6 | 0.41 | <50% | 25.8 |
| 7 | 0.91 | 11.5 | 17.8 |
| 8 | 1.30 | 4.2 | 17.4 |
| 9 | 0.26 | <50% | 10.4 |
| 10 | 1.50 | 14.5 | >50 |
| 11 | 0.59 | 21.2 | >50 |
| 12 | 1.90 | n.p. | >50 |
| 13 | 0.75 | 6.9 | 26.1 |
| 14 | 1.10 | 10.6 | 16.7 |

Table 2 shows the inhibition of HIV-1 RNase H enzymatic activity and the cytopathic effect of α-hydroxytropolones on $HIV-1_{RF}$ virus replication on CEM-SS cells (n.p.=no protective effect on cytopathicity of virus. <50%=protective effect less than 50% of control, i.e. weak activity).

Example 25

The following example depicts the antiviral activity of the compounds in accordance with embodiments of the present invention.

The parent tropolones, β-thujaplicinol and manicol, showed no protection against the cytopathic effect of the virus, with $EC_{50}$ values of 2.3 μM and 13.6 μM (Table 2). Compounds 4 and 12 also showed no protection against virus cytopathicity but were not cytotoxic up to a concentration of 50 μM. Compounds 3, 6, and 9 showed slight protection against cytopathicity. However, in each case, the protection did not reach 50% of control cell growth, and these compounds were therefore judged inactive.

Compounds 1, 2, 5, 7, 8, 10, 11, 13 and 14 all showed protection against the cytopathicity of the virus, with $EC_{50}$ values ranging from about 4.2 μM (Compound 8) to 42.1 μM (Compound 2). In vitro therapeutic indices ($IC_{50}/EC_{50}$) were quite modest, ranging from about 1.2 to 4.9 (Compound 1). The cytotoxicity of all of the active compounds was reduced compared to their manicol precursor.

Example 26

The following example depicts the pyrophosphorolysis/primer rescue assay methods used with the compounds in accordance with embodiments of the present invention.

DNA primers were chain terminated with ddTMP, tenofovir-DP or AZTMP, purified by denaturing polyacrylamide gel electrophoresis and annealed to 2-fold excess of either an RNA or DNA template. About 50 nM of the resulting hybrid was incubated with 250 nM WT HIV-1 or XMRV RT in buffer containing 50 mM Tris-HCl pH 7.8, 50 mM NaCl and 0.2 mM EDTA. For AZT-terminated primers, a "rescue mix" containing 1 μM dTTP/dCTP, 10 μM ddATP and 0.5-1000 μM inorganic pyrophosphate (PPi) was used for the excision reaction. Similarly, for Tenofovir-DP-terminated primers a rescue mix containing 1 μM dATP/dTTP and 10 μM ddGTP and the same range of PPi. Lastly, ddTMP terminated primers were rescued with mix of 1 μM dTTP/dGTP and 10 μM ddCTP in the presence of 500 μM PPi. Non-chain terminated primers were used as a positive control for extension under the same reaction conditions in the absence of a PPi donor. DNA synthesis was initiated by adding $MgCl_2$ to a final concentration of 6 mM and terminated by adding a 2-fold excess of formamide buffer containing bromophenol blue and xylene cyanol. Following denaturation at 95° C. for 5 minutes, products were resolved by denaturing polyacrylamide gel electrophoresis and visualized by phosphorimaging. Results were plotted in Prism 4.0 using the non-linear regression for one site binding using the equation $Y=Bmax*X/(Kd+X)$.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula I:

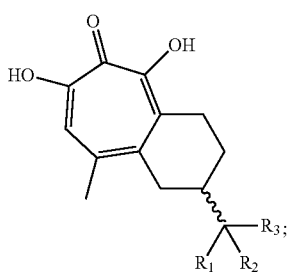

(I)

wherein $R_1$ is selected from the group consisting of H, heterocyclyl $C_1$-$C_6$ alkyl, $C_1$-$C_6$ alkylamino $C_1$-$C_6$ alkyl, $C_1$-$C_6$ dialkylamino $C_1$-$C_6$ alkyl, $C_6$-$C_{14}$ aryl $C_1$-$C_6$ alkylamino, $C_6$-$C_{14}$ aryl $C_1$-$C_6$ alkylamino $C_1$-$C_6$ alkyl, $C_6$-$C_{14}$ aryl amino $C_1$-$C_6$ alkyl, $C_1$-$C_6$ alkylthio $C_1$-$C_6$ alkyl, $C_6$-$C_{14}$ arylthio, $C_6$-$C_{14}$ arylthio $C_1$-$C_6$ alkyl, $C_6$-$C_{14}$ aryl $C_1$-$C_6$ alkylthio $C_1$-$C_6$ alkyl, $C_1$-$C_6$ alkylsulfonyl $C_1$-$C_6$ alkyl, $C_6$-$C_{14}$ arylsulfonyl $C_1$-$C_6$ alkyl, $C_6$-$C_{14}$ arylsulfinyl $C_1$-$C_6$ alkyl, hydroxy $C_1$-$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_6$-$C_{14}$ aryl, $C_6$-$C_{14}$ aryl $C_1$-$C_6$ alkyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl;

$R_2$ is H, OH, or $C_1$-$C_3$ alkyl; and $R_3$ is $C_1$-$C_6$ alkyl; or a pharmaceutically acceptable salt, solvate, stereoisomer, or prodrug thereof.

2. The compound, salt, solvate, stereoisomer, or prodrug of claim 1, wherein $R_1$ is selected from the group consisting of heterocyclyl $C_1$-$C_6$ alkyl, $C_1$-$C_6$ alkylamino $C_1$-$C_6$ alkyl, $C_1$-$C_6$ dialkylamino $C_1$-$C_6$ alkyl, $C_6$-$C_{14}$ aryl $C_1$-$C_6$ alkylamino, $C_6$-$C_{14}$ aryl $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_6$-$C_{14}$ aryl $C_1$-$C_6$ alkylthio $C_1$-$C_6$ alkyl, $C_1$-$C_6$ alkylsulfonyl $C_1$-$C_6$ alkyl, $C_6$-$C_{14}$ arylsulfonyl $C_1$-$C_6$ alkyl, $C_6$-$C_{14}$ arylsulfinyl $C_1$-$C_6$ alkyl, hydroxy $C_1$-$C_6$ alkyl group, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, guanidine, aldehydo, ureido, and aminocarbonyl.

3. The compound, salt, solvate, stereoisomer, or prodrug of claim 1, wherein $R_1$ is $C_1$-$C_6$ dialkylamino $C_1$-$C_6$ alkyl.

4. The compound, salt, solvate, stereoisomer, or prodrug of claim 1, wherein $R_1$ is heterocyclyl $C_1$-$C_6$ alkyl.

5. The compound, salt, solvate, stereoisomer, or prodrug of claim 1, wherein $R_1$ is $C_6$-$C_{14}$ aryl, $C_1$-$C_6$ alkylamino, or $C_1$-$C_6$ alkyl, wherein each of which is optionally substituted with halo.

6. The compound, salt, solvate, stereoisomer, or prodrug of claim 1, wherein $R_1$ is $C_6$-$C_{14}$ aryl amino $C_1$-$C_6$ alkyl.

7. The compound, salt, solvate, stereoisomer, or prodrug of claim 1, wherein $R_1$ is $C_1$-$C_6$ alkylthio $C_1$-$C_6$ alkyl.

8. The compound, salt, solvate, stereoisomer, or prodrug of claim 1, wherein $R_1$ is $C_6$-$C_{14}$ arylthio.

9. The compound, salt, solvate, stereoisomer, or prodrug of claim 1, wherein $R_1$ is $C_6$-$C_{14}$ aryl $C_1$-$C_6$ alkylthio $C_1$-$C_6$ alkyl.

10. The compound, salt, solvate, stereoisomer, or prodrug of claim 1, wherein $R_1$ is $C_1$-$C_6$ alkylsulfonyl $C_1$-$C_6$ alkyl.

11. The compound, salt, solvate, stereoisomer, or prodrug of claim 1, wherein $R_1$ is $C_6$-$C_{14}$ arylsulfinyl $C_1$-$C_6$ alkyl.

12. The compound, salt, solvate, stereoisomer, or prodrug of claim 1, wherein $R_1$ is $C_6$-$C_{14}$ arylsulfonyl $C_1$-$C_6$ alkyl.

13. The compound, salt, solvate, stereoisomer, or prodrug of claim 1, wherein $R_1$ is hydroxy $C_1$-$C_6$ alkyl.

14. The compound, salt, solvate, stereoisomer, or prodrug of claim 1, wherein $R_1$ is H, $R_2$ is OH and $R_3$ is $CH_3$.

15. The compound, salt, solvate, stereoisomer, or prodrug of claim 1, wherein $R_1$ is $C_6$-$C_{14}$ aryl $C_1$-$C_6$ alkylamino, $R_2$ is H and $R_3$ is $CH_3$.

16. The compound, salt, solvate, stereoisomer, or prodrug of claim 1, wherein $R_2$ is OH and $R_3$ is $CH_3$.

17. The compound, salt, solvate, stereoisomer, or prodrug of claim 1, wherein the compound is selected from the group consisting of:

Compound 1
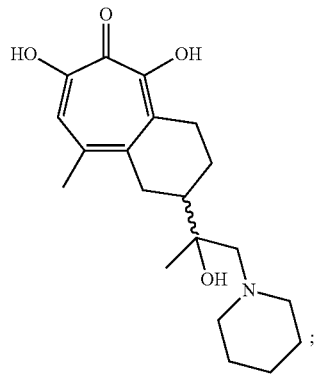

-continued

Compound 2
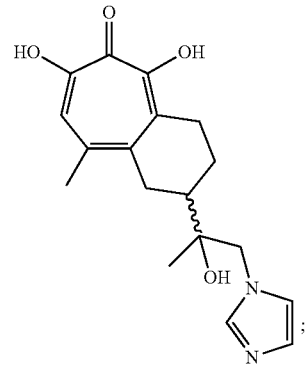

Compound 3
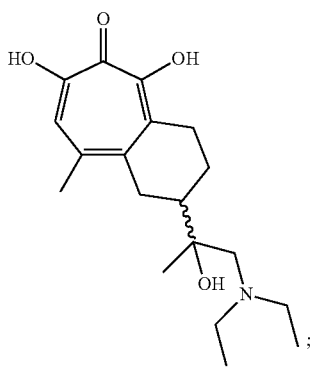

Compound 4
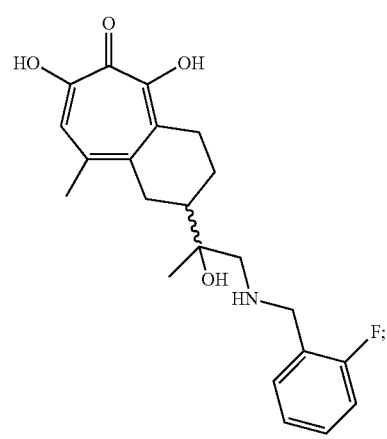

Compound 5
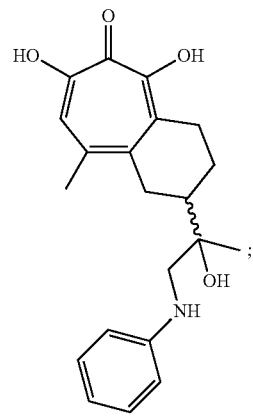

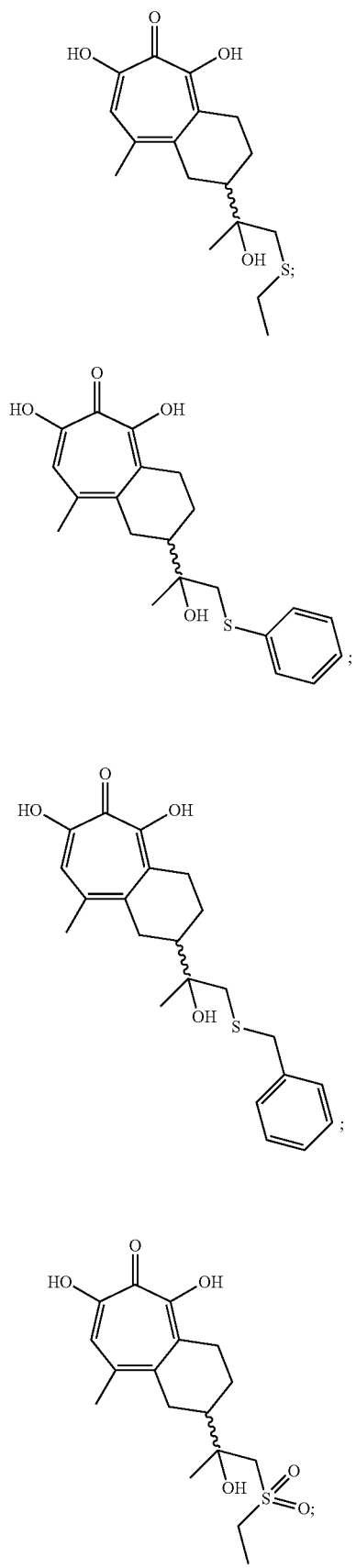
Compound 6
Compound 7
Compound 8
Compound 9
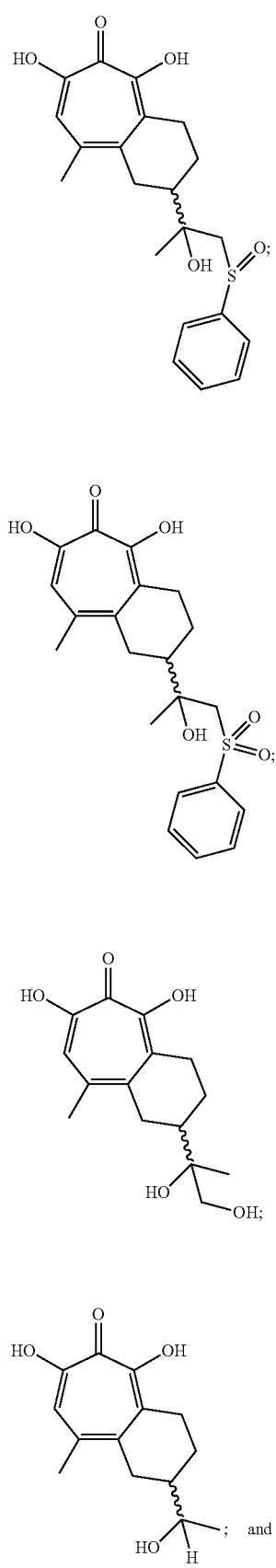
Compound 10
Compound 11
Compound 12
Compound 13
; and Compound 14

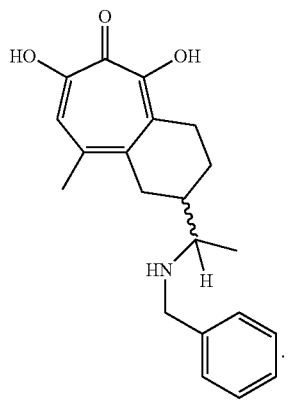

18. A pharmaceutical composition comprising a compound, salt, solvate, stereoisomer, or prodrug of claim 1 and a pharmaceutically acceptable carrier.

19. A pharmaceutical composition comprising at least one compound, salt, solvate, stereoisomer, or prodrug of claim 1 and at least one or more other antiviral compounds and a pharmaceutically acceptable carrier.

20. The pharmaceutical composition of claim 19, wherein the other antiviral compound is selected from the group consisting of nucleoside reverse transcriptase inhibitors (NRTI), non-nucleoside reverse transcriptase inhibitors (NNRTI), integrase inhibitors, fusion inhibitors, and protease inhibitors.

21. A method of treating a retroviral infection in a subject afflicted with a retroviral infection comprising administering an effective amount of a compound, salt, solvate, stereoisomer, or prodrug of claim 1.

22. A method of inhibiting human immunodeficiency virus (HIV) replication in a subject comprising administering an effective amount of a compound, salt, solvate, stereoisomer, or prodrug of claim 1.

23. The method of claim 22, wherein the HIV virus is HIV-1 or HIV-2.

24. A method of inhibiting RNaseH activity of HIV in a subject infected therewith, comprising administering an effective amount of a compound, salt, solvate, stereoisomer, or prodrug of claim 1.

25. A method of inhibiting HIV replication in a host cell infected therewith, comprising contacting the host cell with an effective amount of a compound, salt, solvate, stereoisomer, or prodrug of claim 1.

26. A method of inhibiting RNaseH activity of HIV in a host cell infected therewith, comprising contacting the host cell with an effective amount of a compound, salt, solvate, stereoisomer, or prodrug of claim 1.

* * * * *